United States Patent [19]

Vrancken et al.

[11] 3,952,032

[45] Apr. 20, 1976

[54] COMPOUNDS WITH MULTIPLE ACRYLIC RADICALS, COMPOSITIONS CONTAINING THEM, AND USES THEREOF

[75] Inventors: August Vrancken, Dworp; Paul Dufour, Ruisbroek, both of Belgium; Jacques Noat, Versailles; Jean Holdéric, Asnieres, both of France

[73] Assignee: U.C.B., Societe Anonyme, Brussels, Belgium

[22] Filed: May 14, 1974

[21] Appl. No.: 469,891

[30] Foreign Application Priority Data

May 15, 1973   United Kingdom............... 23083/73

[52] U.S. Cl............................ 260/404.8; 260/407; 260/410.6
[51] Int. Cl.$^2$........................................... C09F 5/00
[58] Field of Search............... 260/404.8, 407, 410.6

[56] References Cited
UNITED STATES PATENTS

| | | | |
|---|---|---|---|
| 2,412,177 | 12/1946 | Schwareman | 260/404.8 |
| 2,723,286 | 11/1955 | Young | 260/404.8 |
| 2,767,144 | 10/1956 | Gottshall | 260/404.8 |
| 2,815,368 | 12/1957 | Motuszak | 260/410.6 |
| 3,000,917 | 9/1961 | Babayan | 260/404.8 |
| 3,035,923 | 5/1962 | Geisler | 260/404.8 |
| 3,586,529 | 6/1971 | Armoff et al. | 260/410.5 |
| 3,676,398 | 7/1972 | D'Alelio | 260/410.5 |

Primary Examiner—Winston A. Douglas
Assistant Examiner—John F. Niebling
Attorney, Agent, or Firm—Wenderoth, Lind & Ponack

[57] ABSTRACT

Compounds with multiple acrylic radicals, the average composition of which has the general formula:

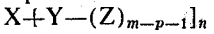

wherein X is the radical derived by removing the OH groups from the carboxyl groups of an organic carboxylic acid containing $n$ COOH groups and the number of carbon atoms of which is between 14 and 90, Y is the radical derived by removing $m$-$p$ hydrogen atoms from the hydroxyl groups of an organic compound containing $m$ OH groups, Z is the monovalent radical derived by removing the OH group from the carboxyl group of a monocarboxylic acid having at least one terminal $CH_2=CH-COO-$ radical, $n$ is a whole number from 1 to 6, $m$ is a whole number from 2 to 8, and $p$ is a number of from 0 to 2.5 with the proviso that $m$-$p$-1 is a positive number different from zero and that $n(m$-$p$-1) is between 2 and 15, processes for the preparation thereof, polymers obtained by polymerization thereof and compositions of matter, in particular UV inks or varnishes, comprising said compounds.

16 Claims, No Drawings

COMPOUNDS WITH MULTIPLE ACRYLIC RADICALS, COMPOSITIONS CONTAINING THEM, AND USES THEREOF

The present invention is concerned with compounds with multiple acrylic radicals, with compositions containing the same and also with processes for their preparation; it is also concerned with the use of these compounds and compositions.

The compounds with multiple acrylic radicals according to the present invention are mixtures, the average composition of which has the general formula $$X-[Y-(Z)_{m-p-1}]_n \quad (I)$$

wherein X is the radical derived by removing the OH groups from the COOH groups of an organic carboxylic acid containing $n$ COOH groups and the number of carbon atoms of which is between 14 and 90 and preferably between 18 and 54.

Y is the radical derived by removing m-p hydrogen atoms from the hydroxyl groups of an organic compound containing $m$ OH groups, Z is the monovalent radical derived by removing the OH group from the COOH group of an organic monocarboxylic acid containing at least one terminal $CH_2=CH-COO-$ radical, $n$ is a whole number of from 1 to 6 and preferably of from 1 to 4, $m$ is a whole number of from 2 to 8 and preferably of from 3 to 6, and $p$ is a number of from 0 to 2.5 with the proviso that m-p-1 is a positive number different from zero and that n(m-p-1) is between 2 and 15.

It is essential that the organic carboxylic acid, the radical of which is designated X in the above general formula, has the hydrophobic character of a higher fatty acid; it is for the reason that it contains 14 to 90 carbon atoms and preferably 18 to 54 carbon atoms. The organic carboxylic acid radical may be saturated or unsaturated and straight or branched; in addition, it contains from 1 to 6 and preferably from 1 to 4 carboxyl groups. Instead of the free acid, it is also possible to use functional derivatives, such as acid halides, anhydrides, esters, salts or the like. However, according to the invention, for certain applications, it is also possible to replace up to 75 mole percent of the organic carboxylic acid containing at least 14 carbon atoms by one or more mono- or polycarboxylic acids containing less than 14 carbon atoms, such as adipic acid, maleic anhydride, HET acid, tetrabromophthalic anhydride, isophthalic acid or the like.

Examples of monocarboxylic acids XOH ($n = 1$) which can be used in the compounds of the present invention include the saturated and unsaturated monocarboxylic fatty acids containing at least 14 carbon atoms, such as myristic acid, palmitic acid, stearic acid, arachidic acid, behenic acid, lignoceric acid, cerotic acid, montanic acid, oleic acid, ricinoleic acid, linoleic acid and linolenic acid; mixtures of fatty acids originating from vegetable fats, such as palm oil, linseed oil, dehydrated or non-dehydrated castor oil, perilla oil, soya oil, safflower oil, Chinese wood oil oiticica oil, cotton seed oil, tall oil and the like; mixtures of fatty acids originating from animal fats, such as tallow, lard, whale oil, fish oils and the like; and saturated and unsaturated synthetic fatty acids having the number of carbon atoms indicated above.

Examples of dicarboxylic and polycarboxylic acids $X(OH)_n$ ($n = 2$ to 6) which can be used in the compounds of the present invention are the dimerized and trimerized fatty acids derived from fatty acids containing two or three double bonds, such as the Empol commercial products of the firm Emery Industries, Inc. and the Hystrene products of the firm Hunco Chemical Products Ltd., the dimer of methyl linoleate, the chlorides of these dimers, lower dicarboxylic acids carrying a long chain hydrocarbon radical, for example dodecyl-, tetradecyl-, hexadecyl- and octadecyl- succinic acids and the like, and also the lower dicarboxylic acids carrying a thiohydrocarbon radical, for example dodecylthiosuccinic acid and the like; the Diels-Alder addition products of maleic anhydride with a fatty acid or a drying oil containing conjugated double bonds, for example conjugated linoleic acid, alpha or beta-eleostearic acid, China wool oil, oiticica oil and the like; the reaction products of maleic anhydride with fatty acids or oils containing one or more non-conjugated double bonds; the reaction products of polycarboxylic acids or their anhydrides (maleic, succinic, phthalic, trimellitic, pyromellitic acids and anhydrides and the like) with hydroxylated long chain compounds, for example ricinoleic acid, higher fatty alcohols, epoxidized higher fatty acids, oils containing hydroxylated higher fatty acids, for example castor oil, or epoxidized natural oils; polycarboxylic acids prepared from an alkyd resin containing higher fatty acid radicals and an excess of di- or polycarboxylic acid, which consequently are alkyd resins in carboxyl groups, the alkyd resins rich in carboxyl groups obtained by condensing a dimer or trimer acid containing at least 14 carbon atoms and a diacid having a chain which is shorter than 14 carbon atoms with a polyhydroxylated compound; the addition products of lower to higher mono- or polycarboxylic mercapto acids with unsaturated fatty acids, oils or alkyd resins, such as the addition product of mercaptobutyric acid with linseed oil, the addition product of thioglycolic acid with linolenic acid and the like; brassylic acid (High Polymers, vol.27, Wiley-Intersciences, p.88-91); the dicarboxylic acids having 19 carbon atoms obtained by the KOCH synthesis, the OXO synthesis of ROELEN and the REPPE reaction (High Polymers, vol.27, Wiley-Intersciences, p.97-110); and the like.

The organic compound, the radical of which is designated Y in the above general formula contains from 2 to 8 and preferably from 3 to 6 hydroxyl groups in the molecule. It can be a diol, such as ethylene glycol, propylene glycol, 1,4-, 1,3-, or -2,3-butane-diol, 1,6-hexane-diol, neopentyl glycol, diethylene glycol, dipropylene glycol, dibutylene glycol, the polyethylene glycols, the polypropylene glycols or the like. However, the hydroxylated compound preferably contains at least 3 hydroxyl groups, examples of these including glycerol, trimethylolethane, trimethylolpropane, pentaerythritol, dipentaerythritol, tripentaerythritol, sorbitol, mannitol, inositol, pinitol, quebrachitol, alpha-methylglycoside and the like, as well as the hydroxylated products obtained by the condensation of ethylene or propylene oxide with aforesaid polyalcohols. It is also possible to use polyhydroxylated polymers, such as polyether alcohols and polyester alcohols as well as their oxyalkylation products with ethylene oxide or propylene oxide.

The organic monocarboxylic acids containing at least one terminal $CH_2=CH-COO-$ radical providing the monovalent radical Z include, for example, acrylic acid, the reaction product of one mole of a saturated or unsaturated dicarboxylic acid or anhydride with one mole of a hydroxyalkyl acrylate, for example the reaction product of 2-hydroxyethyl acrylate, 2-hydroxypropyl acrylate, 4-hydroxybutyl acrylate, 6-hydroxyhexyl acrylate, 8-hydroxy-octyl acrylate, 10-hydroxydecyl acrylate, 12-hydroxydodecyl acrylate or the like with succinic anhydride, maleic anhydride, phthalic anhydride, adipic acid, sebacic acid, itaconic acid or the like; the reaction product of two moles of a hydroxyalkyl acrylate with one mole of a triboxylic acid or anhydride, such as trimellitic anhydride, aconitic acid or citric acid; the reaction product of three moles of a hydroxyalkyl acrylate with one mole of a tetracarboxylic dianhydride or acid, such as pyromellitic anhydride or acid, or any other organic compound containing at the same time at least one free carboxyl group (or the chemical equivalent of a carboxyl group, such as an acid halide, anhydride, ester, salt or similar group) and at least one terminal $CH_2=CH-COO-$ radical.

For the preparation of compounds with multiple acrylic radicals corresponding to the above general formula, various processes are available.

One-stage process (Process No. 1)

Stoichiometric quantities of the constituents providing the radicals X, Y and Z in the above general formula (i.e. one mole of the higher organic carboxylic acid $X(OH)_n$, n moles of the organic compound $YH_m$ and $n(m-1)$ moles of the monocarboxylic acid ZOH with at least one terminal $CH_2=CH-COO-$ radical) are heated in an organic, water-entraining sovent (benzene, toluene or the like) in the presence of a radical polymerization inhibitor (hydroquinone, cuprous oxide or the like), an esterification catalyst (sulfuric acid, p-toluene-sulfonic acid or the like) and optionally an additive preventing the coloration of the products obtained (for example triphenyl phosphite or the like). The reaction can be carried out at atmosphere pressure, advantageously in an inert atmosphere (nitrogen or the like) at a temperature of about 70°–140°C., for a period of 2 to 10 hours with removal of the water of esterification with the aid of the solvent.

The reaction is stopped as soon as the desired degree of esterification (measured in accordance with the amount of water of esterification collected) has been reached.

After having eliminated in known manner the solvent, the catalyst, excess inhibitor and any excess of monocarboxylic acid ZOH containing at least one terminal $CH_2=CH-COO-$ radical, a product of the present invention is obtained, which can be used, either untreated or after a suitable purification, for its various applications.

The reaction product thus obtained is a mixture of compounds having a given molecular weight distribution, as can be shown by gel permeation chromatography, the average composition of which, however, has the general formular I given above. The products of the invention have a well defined content of hydroxyl groups. In formula I, p represents the average number of free hydroxyl groups which remain unreacted in the end product after esterification.

This one stage process is preferred for reasons of simplicity of operation and economy. However, similar end products with an average composition of the formula I given above can be obtained by one of the following two-stage processes.

Two-stage processes (Processes Nos. 2a and 2b).

a. Under esterification conditions similar to those described for the single-stage process, the organic compound $YH_m$ is first esterified with the higher organic carboxylic acid $X(OH)_n$, whereupon the residual hydroxyl groups of the organic compound $YH_m$ are esterified with the monocarboxylic acid ZOH containing at least one terminal $CH_2=CH-COO-$ radical.
b. Alternatively, the organic compound $YH_m$ is first esterified with the monocarboxylic acid ZOH, only one hydroxyl group preferably being allowed to remain in the organic compound $YH_m$, whereupon the latter is esterified with the higher organic carboxylic acid $X(OH)_n$.

In the single-stage or two-stage processes described above, the free acids $X(OH)_n$ and ZOH may be replaced by the halides, preferably chlorides, or anhydrides of these acids. Particularly in the case of acid halides, this makes it possible to carry out the esterification at more moderate temperatures, for example below about 40°C.; in this case, it is advantageous to carry out the esterification in the presence of an acid acceptor, such as pyridine, triethylamine or the like.

In addition, the compounds of the present invention can also be obtained by transesterification of the organic compound $YH_m$ with lower alkyl esters of the acids $X(OH)_n$ and ZOH. In this case, the transesterification is carried out in a solvent having a sufficiently high boiling point (for example toluene or the like) to ensure that the reaction takes place at the boiling temperature of the mixture at an adequate speed and that an azeotropic mixture is formed with the lower alcohol freed by the transesterification. The rate of transesterification is monitored by measuring the amount of lower alcohol thus liberated, which is collected.

In the Table I given below some non-limitative examples are given of the compounds with multiple acrylic radicals according to the present invention. The Table shows the number of the compound with multiple acrylic radicals, the nature and the molar proportion of each of the constituents X, Y and Z, together with the number of the preparation process (1 = single-stage process; 2a = two-stage process with reaction first between $X(OH)_n$ and $YH_m$; 2b = two-stage process with reaction first between $YH_m$ and ZOH).

The abbreviations used in this Table have the following meanings:
ADA: adipic acid
MA: maleic anhydride
PA: phthalic anhydride
HEA: hydroxyethyl acrylate
HPA: 2-hydroxypropyl acrylate
(ADA + HEA): addition product of adipic acid and hydroxyethyl acrylate
(MA + HEA): addition product of maleic anhydride and hydroxyethyl acrylate
(PA + HEA): addition product of phthalic anhydride and hydroxyethyl acrylate
(MA + HEA): addition product of maleic anhydride and 2-hydroxypropyl acrylate
dimer acid =
 EMPOL (Emery Industries Inc.) : the dicarboxylic dimerization products of $C_{18}$ unsaturated monobasic fatty acids. The reaction of dimerization may however leave a certain percentage of unpolymerized monobasic acid and/or produce a certain percentage of trimer acid. According to the composition of the dimer obtained, several commercial products are characterized by a number following the Registered Trade Mark EMPOL. Thus EMPOL 1010 is the purest commercial dibasic $C_{36}$ dimer, containing only 3% trimer and no monobasic acid;

EMPOL 1022 is a dimer acid containing 19–22% trimer and 5% monobasic acid;

EMPOL 1038 is the same as the preceding one but less coloured. Dimer acid chloride : acid chloride of EMPOL PLURACOL SP 760: addition product of about 12 moles of ethylene oxide on 1 mole of sorbitol, having a molecular weight of about 700

PLURACOL PeP 450: addition product of about 7 moles of ethylene oxide on 1 mole of pentaerythritol having a molecular weight of about 400

TERCAROL G 310 (glycerol + 3 moles propylene oxide, molecular weight about 310)

tetracid: esterification product of one mole of pyromellitic acid with 4 moles of ricinoleic acid.

triacid: addition product of 2 moles of thioglycolic acid on 1 mole of linolenic acid.

poises. They are colourless to dark brown compounds, depending upon the quality of the raw materials and the operating conditions used in the course of the synthesis. They have a good solubility in aromatic solvents, ketones, esters and the like, as well as in mono- and polyfunctional vinylic and acrylic monomers. Their vapour pressure at ambient temperature is practically negligible. Their hydrophobic character is more or less pronounced, depending upon the raw materials used for their preparation.

The present invention is also concerned with the reaction products obtained by reacting the mixture of compounds with the average composition of formula (I) given above, wherein p is more than zero, with aliphatic, cycloaliphatic, heterocyclic or aromatic mono- or di-isocyanates. The properties of the urethane-modified products thus obtained differ from the non-modified starting products by a higher viscosity and a lower hydroxyl number. Photopolymerizable inks and overprint varnishes formulated with these modified resins dry at higher rates than the corresponding unmodified products. Due to an improvement of the rheological properties and a better equilibration of the hy-

TABLE I

| Compound No | Constituent X | moles of X | Constituent Y | moles of Y | Constituent Z | moles of Z | Process |
|---|---|---|---|---|---|---|---|
| 1 | ricinoleic acid | 1 | trimethylopropane | 1 | acrylic acid | 3 | 1 |
| 2 | stearic acid | 1 | sorbitol | 1 | (ADA + HEA) | 5 | 1 |
| 3 | oleic acid | 1 | dipentaerythritol | 1 | (MA + HEA) | 5 | 1 |
| 4 | linseed fatty acid | 1 | Pluracol SP 760 | 1 | (PA + HEA) | 5 | 1 |
| 5 | dimer acid (EMPOL 1010) | 1 | pentaerythritol | 2 | acrylic acid | 6 | 1 |
| 6 | dimer acid (EMPOL 1010) | 1 | Tercarol G 310 | 2 | acrylic acid | 4 | 1 |
| 7 | (MA + linoleic acid-9,12) | 1 | ethylene glycol | 3 | (MA + HPA) | 3 | 1 |
| 8 | tetracid | 1 | trimethylolpropane | 4 | acrylic acid | 8 | 1 |
| 9 | dimer acid (EMPOL 1010) | 1 | glycerol + 12 moles ethylene oxide | 2 | (MA + HEA) | 4 | 1 |
| 10 | dimer acid chloride | 1 | pentaerythritol | 2 | acryloyl chloride | 6 | 1 |
| 11 | (MA + linoleic acid-9,12) | 1 | Tercarol G 310 | 3 | acrylic anhydride | 3 | 1 |
| 12 | methyl linoleate dimer | 1 | glycerol | 2 | ethyl acrylate | 4 | 1 |
| 13a = | oleic acid | 1 | Pluracol SP 760 | 1 | | | |
| 13b | 13a | | + | | acrylic acid | 5 | 2a |
| 14a | stearic acid | 1 | Pluracol PeP 450 | 1 | | | |
| 14b | 14a | | + | | (MA +HEA) | 3 | 2a |
| 15a = | | | sorbitol + 12 moles ethylene oxide | 1 | acrylic acid | 5 | 2b |
| 15b | oleic acid | 1 | + 15a | | | | |
| 16 | triacid | | polyethylene glycol | 3 | acrylic acid | 3 | 1 |
| 17a = | | | pentaerythritol | 2 | acrylic acid | 6 | 2b |
| 17b | dimer acid (EMPOL 1010) | 1 | + 17a | | | | |

Two remarks have to be made regarding the above Table:

1. The respective molar proportions of the constituents X, Y and Z used for the preparation of the compounds with multiple acrylic radicals according to the present invention were established with due regard to the number of carboxyl groups and hydroxyl groups present in these three constituents. Nevertheless, important deviations may be admitted in respect of these proportions, while still obtaining products within the scope of the present invention.

2. The end products obtained from the same starting materials by the different processes mentioned above present a different molecular weight distribution as can be shown by gel permeation chromatography. The products obtained by the two-stage processes present a broader molecular weight distribution than the products obtained by the one-stage process.

The compounds with multiple acrylic radicals according to the present invention are liquid to waxy substances, the viscosity of which at ambient temperature is between a few poises and several hundred drophobic/hydrophylic balance in the molecule, ultra-violet drying offset formulations, comprising said urethane-modified products, have a better printing behaviour on high speed printing presses. Mechanical properties and chemical resistance of the cured film are improved on using the urethane-modified products.

As non-limiting examples of isocyanates, mention may be made of the following monoisocyanates: methyl-isocyanate, ethyl-isocyanate, propyl-isocyanate, butyl-isocyanate, cyclohexyl-isocyanate and phenyl-isocyanate; the following diisocyanates: hexamethylene-diisocyanate, trimethylhexyl-diisocyanate, dimer fatty acid-diisocyanates such as DDI produced by General Mills Chemicals, isophorone-diisocyanate, dicyclohexylmethane-diisocyanate, toluylene-diisocyanate and diphenylmethane-4,4'-diisocyanate; and urethanized adducts obtained by reacting diisocyanates with monoalcohols.

In a preferred embodiment for the preparation of these urethane-modified compounds, from 2 to 20% by weight of mono- or diisocyanates are progressively added to the compounds with the average composition of formula (I) given above, in the presence of known catalysts, such as dibutyl-tin dilaurate, triethylene diamine etc. The reaction is carried out between 40° and 80°C., preferably between 55° and 70°C., optionally in the presence of inert solvents. In order to allow a certain number of unreacted hydroxyl groups to remain in the end product, the molar ratio of isocyanate to hydroxyl groups in the reacting products is chosen below unity. In order to lower the viscosity, it is possible, for example, to reduce the molecular weight of the compounds of the present invention by partial transesterification, in known manner, with a mono- or polyalcohol, such as methanol, ethanol, ethylene glycol, hydroxyalkyl acrylate or the like having a molecular weight below 200.

Because of the presence of a plurality of acrylic unsaturation groups in their molecules, the compounds according to the present invention are readily polymerizable and can form three-dimensional cross-linked polymers under the following conditions: by the action of heat at a temperature between 50° and 250°C, preferably between 50° and 150°C., preferably in the absence of oxygen; by the addition of radical initiators which decompose at a higher temperature (for example above 40°C.) or even at ambient temperature, provided that an accelerator is added; by exposure to ionizing radiation of electromagnetic nature (gamma-rays or X-rays) or of corpuscular nature (accelerated electrons), even in the presence of air and without any additive being necessary; in visible and or ultra-violet light, provided that a photosensitizer or photoinitiator is added.

The compounds with multiple acrylic radicals according to the present invention may, therefore, advantageously be used as film-forming binders for all applications where rapid polymerization is required; being used either singly or mixed with other materials, such as inert noncopolymerizable polymers; reactive copolymerizable polymers; copolymerizable oligomers; inert plasticizers; inert organic solvents; copolymerizable olefinically-unsaturated monomer compounds and various adjuvants.

As examples of inert polymers, mention may, in particular, be made of the following: polyolefins, polystyrene, polyalkyl acrylates, polyvinyl chloride, polyvinyl acetate, polyethers, polyamides, saturated polyesters, alkyd resins, epoxy resins, urea-formaldehyde resins, arylsulfonamideformaldehyde resins, terpene-phenol resins, polyvinyl alkylethers, chlorinated rubber, cellulose esters (acetopropionate, acetobutyrate or the like), copolymers of vinyl chloride with vinyl acetate, maleic esters, vinylidene chloride, vinyl esters or the like.

As examples of reactive copolymerizable polymers, mention may be made of the unsaturated polyesters and unsaturated alkyd resins, the unsaturated resins obtained by reacting an unsaturated hydroxylated compound (for example allyl alcohol, hydroxyethyl acrylate or the like) with the addition product of a polyisocyanate (for example tolylene diisocyanate, hexamethylene diisocyanate or the like) and a resin having free hydroxyl groups (for example a hydroxylated polyester, a hydroxyalkyl acrylate copolymer, a hydroxylated polyether or the like), this addition product still containing free NCO groups. As examples of other reactive resins which can be used according to the present invention, reference is, in particular, made to the article by A. Vrancken, XIth Fatipec Congress, June 11–16, 1972, Florence, pages 19 to 41.

The copolymerizable oligomers which can be added to the polymerizable compounds according to the present invention are principally used when it is required to modify the viscosity, the flow limit or the tack, for the purpose of adapting the resulting product to various applications and/or technical utilisations. They are especially used for lowering the viscosity of the product obtained. At the moment of polymerization, these oligomers copolymerize with the compounds according to the present invention and thus finally form part of the compositions thus obtained. Examples of copolymerizable oligomers include the di-, tri- and polyacrylates of hydroxylated products obtained by condensing ethylene oxide or propylene oxide with glycerol, trimethylolpropane, pentaerythritol, sorbitol or the like.

The inert plasticizers which can be added to the compounds with multiple acrylic radicals of the present invention can be esters of organic or mineral acids, such as o-, iso- or terephthalic acid, adipic acid, azelaic acid, sebacic acid, citric acid or phosphoric acid, with mono- polyhydroxylated aliphatic and aromatic hydroxylated compounds, such as butanol, 2-ethylhexanol, phenol, cresol, diethylene glycol, triethylene glycol, dipropylene glycol or the like. It is also possible to use epoxidized oils, chlorinated paraffins, chlorinated polyphenyls, chlorinated naphthalenes or the like as plasticizers.

If desired, it is possible to add inert organic solvents, such as ethyl acetate, methyl ethyl ketone or the like, to the compounds with multiple acrylic radicals of the present invention, these solvents being mainly added in order to lower the viscosity. Nevertheless, it is preferable not to use solvents because the problems of recovery, intoxication and pollution caused by solvents are thus eliminated. As mentioned above, according to the present invention, it is, in fact, possible for the viscosity of the compositions prepared from the compounds with multiple acrylic radicals of the present invention to be regulated at will, so that the viscosity may vary from a few poises to several thousand poises at 25°C., thus making the use of organic solvents unnecessary.

On the other hand, it may be advantageous for copolymerizable olefinically-unsaturated monomer compounds to be used with the compounds of the present invention. Depending upon the intended use, these monomers may or may not be volatile and may contain one or more olefinically-unsaturated bonds. Examples of these copolymerizable olefinically-unsaturated compounds include styrene, vinyl acetate, vinyl chloride, vinylidene chloride, the mono-, di- and polyacrylates of di-, tri- and polyols, such as trimethylolpropane triacrylate, pentaerythritol tri- and tetraacrylate and the like. Like the copolymerizable oligomers mentioned previously, the copolymerizable olefinically-unsaturated monomer compounds may be added to the compounds with multiple acrylic radicals of the present invention in order to modify their viscosity and in copolymerized form they will form part of the final polymer products thus obtained.

The following examples are given of adjuvants which can be added to the compounds according to the present invention: known heat and light stabilizers, known antioxidizing agents; known viscosity modifying agents or thixotropic agents, known flow agents, chain transfer agents serving to accelerate the radical polymerization once it has been started (examples of these agents include di- and triamines, alkanolamines, monoalkyldialkanolamines and dialkylmonoalkanolamines, morpholine and its derivatives, polyamines, N-phenylglycine and its derivatives, N,N'-dimethylmonoethanolamine monoacrylate, N-methyldiethanolamine diacrylate, triethanolamine triacrylate, and the like); polymerization inhibitors intended to provide stability during storage (for example quinones, hydroquinones, substituted phenol derivatives, primary aromatic amines, copper compounds and the like); waxes, the purpose of which is to assist the obtaining of non-scratching hardened films, which waxes may be natural, such as candelilla wax, Carnauba wax or the like, or synthetic, such as polyethylene, polypropylene or paraffin wax, chlorinated paraffins, chlorinated naphthalenes or the like; pigments, dyes, mineral or organic fillers, fibrous or pulverulent reinforcing agents, and the like.

The compounds according to the present invention can be used for various purposes, some non-limitative examples of which are given below:

By the addition of radical initiators (peroxides, hydroperoxides, percarbonates, azo compounds or the like) decomposing under the influence of heat, the compounds of the present invention can be used as casting, compression moulding, injection moulding and extrusion resins. Because of the excellent flexibility of the products obtained according to the present invention, they may be added to polyvinyl chloride plastisols at the rate of 5–30% by weight of the total composition, as reactive plasticizers to assist adhesion to metal sheets and to increase the cohesive force of the film applied.

By the addition of accelerators to some of the initiators described above, for example by adding dimethyl-p-toluidine to benzoyl peroxide, cobalt naphthenate to methyl ethyl ketone peroxide or the like, the polymerization of the compositions according to the present invention can be initiated at ambient temperature. Compositions of these formulations may be used, in particular, as road marking paints. In this particular case, paraffin is added to the formulations so that, after application to the substrate, the paraffin separates out and forms a surface film providing protection against the action of atmospheric oxygen. Another typical application of the compositions according to the present invention is as anaerobic adhesives in which the initiator-accelerator pair is appropriately selected. These compositions have the property of not polymerizing in the presence of air, so that they can be stored for several months at ambient temperature. If, however, the presence of oxygen is excluded, these adhesives start to polymerize slowly. Furthermore, the presence of metallic ions, such as iron ions, has the effect of considerably increasing the speed of polymerization, so that they can be used for locking metallic connections under anaerobic conditions.

In the complete absence of initiators, accelerators and the like, the compositions according to the present invention can be polymerized extremely rapidly by accelerated electron beam curing. They can, therefore, be used for the production of varnishes, paints, coatings or the like and serve for the industrial coating of a large variety of substrates, including particule wood boards, chip boards, fibre boards, hardboard, paper, metal, asbestos-cement and the like.

If photosensitizers and/or photoinitiators are added to the compositions of the present invention, compositions are obtained which can be polymerized under the influence of light having one or more wavelengths between 200 nm and 5000 nm. The photosensitizers supply to all the molecules containing one or more unsaturations or to the initiator, part of the energy transmitted by the light. By means of the unsaturated system or systems or of a photoinitiator, the photosensitizers produce free radicals or ions which initiate the polymerization or the cross-linking of the composition.

With regard to the photosensitizers or photoinitiators which can be used according to the present invention, the following references are in particular quoted: G. Delzenne, Ind.Chim.Belge, 24, 739–764/1959; J. Kosar, "Light Sensitive Systems", pub. Wiley, New York, 1965; N. J. Turro, "Molecular Photochemistry", pub. Benjamin Inc., New York, 1967; H. G. Heine et al., Angew.Chem.84, 1032/1972.

The photoinitiators are essentially chemical substances belonging to one of the following major categories: compounds containing carbonyl groups, such as pentanedione, benzil, piperonal, benzoin and its halogenated derivatives, benzoin ethers, anthraquinone and its derivatives, p,p'-dimethylaminobenzophene, benzophenone and the like; compounds containing sulfur or selenium, such as the di- and polysulfides, xanthogenates, mercaptans, dithiocarbamates, thioketones, betanapthoselenazolines; perioxides; compounds containing nitrogen, such as azonitriles, diazo compounds, diazides, acridine derivatives, phenazine, quinoxaline, quinazoline and oxime esters, for example 1-phenyl-1,2-propanedione 2-[0-(benzoyl)oxime]; halogenated compounds, such as halogenated ketones or aldehydes, nethylaryl halides, sulfonyl halides or dihalides; and photoinitiator dyestuffs, such as diazonium salts, azoxybenzenes and derivatives, rhodamines, eosines, fluoresceines, acriflavine or the like.

The photosensitizers belong to one of the following categories: ketones and their derivatives, carbocyanines and methines, polycyclic aromatic hydrocarbons, such as anthracene or the like, and dyestuffs, such as xanthenes, safranines and acridines.

After the addition of 0.1 to 10% by weight of photoinitiators and/or photosensitizers, the products of the present invention or mixtures containing these products can be used for the production of transparent varnishes for coating a large variety of substrates, for example those which have been mentioned above for the polymerization by accelerated electron beams.

They can also be used for the production of semi-transparent sealers having a high content of transparent fillers and coloured sealers containing dyestuffs which are transparent to part of the emission spectrum of the lamp. The fillers are selected so as to have a minimum absorption at the wavelengths of from 200 to 700 nanometers of the spectrum. They include, in particular, precipitated or micronized calcium or magnesium carbonate (calcite, aragonite or the like), barium or calcium sulfate (baryta, blanc fixe or the like), micronized hydrated potassium or magnesium silicoaluminate, micronized magnesium silicate, precipitated hydrated alumina, asbestine, micronized or non-micronized talc and the like.

The photopolymerizable compositions of the present invention can also be used as laminating or composite bonding glues for bonding safety glasses, laminated packing films or composites, provided that at least one element of the bonded material is transparent to ultraviolet radiation.

They can also be used in printed circuits, relief and gravure printing plates, photoreproduction, photoresists and the like.

A particularly advantageous field of use for the compounds of the present invention is for solventless ultra-violet inks, i.e., inks which dry and harden under the action of ultra-violet rays. In this particular case, very thin pigmented or coloured coats of these inks are applied, which, because of the low thickness applied, allow penetration of ultra-violet radiation to a sufficient depth to initiate photopolymerization at a very high initiation speed.

Solventless inks are of interest in connection with the fight against pollution. Conventional printing inks contain up to 45% of hydrocarbons which are eliminated in ovens. The solvents are discharged to the atmosphere, together with the combustion gases. This can be avoided by the expensive installation of catalytic or thermal postcombustion devices. However, in the case of accidental stoppage of the press, the paper in the ovens might ignite, thus giving rise to a risk of fire and considerable expense for re-starting.

The use of ultra-violet inks reduces the overcrowding of a workshop equipped with sheet-fed presses. Dried ultra-violet inks have greater mechanical strength and chemical resistance, while the speed of drying is considerably increased, thus leading to a reduction of waiting before finishing off, with a reduction of stocks of printed material in the course of production and the elimination of the use of anti setoff powders, which give rise to premature wear of certain parts of the press and entail difficulties in subsequent finishing, for example film lamination.

The drying of inks, varnishes or lamination bonding products by ultra-violet irradiation is a known technique which has been described in numerous patents. Nevertheless, the quality of products available on the market has retarded their adoption by the graphic arts industry. In particular, some known ultra-violet inks have insufficient storage stability or unsatisfactory drying properties, while others have good drying properties but, to a still greater extent than the first inks mentioned, entail considerable difficulties in obtaining the water/ink balance in the offset process, which difficulties may even entail scumming or pronounced tinting. Furthermore, reproducibility with various manufacturing batches must be considered as inadequate because of the absence of definitions of chemical and physical characteristics (or control standards) which must be respected by the unsaturated prepolymers and unsaturated monomers and/or oligomers used in the composition of these inks.

The products of the present invention are prefectly suitable for the production of offset, letterpress and flexographic inks and also for inks used for copperplate printing, gravure and silk screen printing, which dry under ultra-violet radiation.

The composition of inks and varnishes, which are photopolymerizable by ultra-violet rays (abbreviated as UV inks) of the present invention can be as follows:

The polymerizable binder for the ultra-violet inks and varnishes according to the present invention comprises 5 to 100% by weight of at least one compound with multiple acrylic radicals of the present invention and 0 to 95% by weight of at least one compound selected from the group consisting of (a) copolymerizable reactive unsaturated polymers, (b) copolymerizable unsaturated oligomers, and (c) copolymerizable unsaturated monomers, examples of constituents (a), (b) and (c) having already been given in the above description.

In order to obtain quickly drying UV inks, the compounds with multiple acrylic radicals of the present invention should average 2 to 15, preferably 4 to 9 $CH_2=CH-COO-$ groups per molecule.

Among these compounds (a), (b), (c), the compounds selected will be those which have a good compatibility with the compounds with multiple acrylic radicals of the present invention and a comparable level of polymerization reactivity. These compounds are generally used for modifying the rheology of the inks or for improving adherence, for example in the case of printing on tin plate, on aluminium, on sheets of plastics material or the like. Compounds (b) and (c) are used mainly for the purpose of lowering the viscosity of inks. The monomers (c) are preferably selected from compounds having negligible volatility at 25°C. and a high acrylic radical content, for example trimethylolethane triacrylate, trimethylolpropane triacrylate, glycerol triacrylate, butane-1,2,4-triol triacrylate, pentaerythritol tri- or tetraacrylate, dipentaerythritol tetra-, penta- or hexaacrylate or the like.

The inert polymers and plasticizers of the ultra-violet inks according to the present invention are selected from the products which have already been mentioned above in the description, care being taken to ensure good compatibility with the photopolymerizable binder and the other constituents of the ink, the absence of chemical interaction with the other constituents of the ink and low absorption in the ultra-violet spectrum.

The inert polymers are added to adapt or modify the printability characteristics, the final appearance (gloss) and the properties of the ink films obtained. The plasticizers are used, in particular, in order to solubilize the photoinitiator and/or the photosensitizer or other adjuvants.

The pigments and fillers for the ultra-violet inks according to the present invention are added in order to impart colorimetric properties. An ink or a varnish may contain 0 to 30%, preferably between 0 and 18%, of organic pigments which are transparent and semi-transparent to ultra-violet rays, 0 to 60% of hiding mineral pigments, and 0 to 50% of fillers transparent to ultra-violet rays, the total amount of fillers and pigments being between 10 and 60% in the case of ultra-violet inks and 0% in the case of overprinting. These pigments and fillers must neither retard nor inhibit the photopolymerization of the photopolymerizable binder. They must neither react chemically with the photoinitiator or

| | |
|---|---|
| photopolymerizable binder | 10–90% by weight |
| inert polymers and plasticizers | 0–40% by weight |
| pigments and fillers | 0–60% by weight |
| photoinitiators and/or photosensitizers which are active at the wavelengths of 100 to 400 nanometers | 1–15% by weight |
| conventional additives for UV inks | 1–10% by weight | photoinitiators and/or photosensitizer or photosensitizers, nor may they adsorb them physically.

The organic pigments can be selected from those products listed in the Colour Index, the absorption of which at wavelengths of 200 to 500 nanometers is as low as possible.

The utilization of opacifying or hiding mineral pigments may become necessary for the production of white inks, which is the case, for example, with offset inks intended for printing on tin plate. As examples of opacifying pigments, there may be mentioned titanium, zinc, iron or chromium oxides, zinc or cadmium sulfides; manganese or ammonium phosphates; cobalt aluminates or the like. It is obvious that the absorption of ultra-violet rays by these opacifying pigments is higher than with organic pigments which are transparent to ultra-violet rays and that inks formulated with these opacifying pigments necessitate higher irradiation energy (expressed in milliwatts per square centimeter of printed surface). In other words, in order to obtain the same drying rate, the number of ultra-violet radiators must be increased.

The fillers which are transparent to ultra-violet rays and intended for the inks according to the present invention, which have already been mentioned above in the description relating to sealers, may be added in order to modify the rheological behaviour of the ink.

The photoinitiators and photosensitizers and also the various additives suitable for ultraviolet inks have already been mentioned above in the description.

The compounds according to the present invention are characterized by a balance of the lipophilic and hydrophilic parts of the molecule which makes them particularly suitable for use for the formulation of ultra-violet offset inks. Unlike the binding agents used at the present time in ultra-violet offset inks, the balance between ink and dampening solution can easily be achieved and maintained on the press, even after a halt in the printing, when the compounds according to the present invention are used. Isopropanol contents of the order of 15–20% may be used, without difficulty, in continuous dampening systems. Of the compounds of the present invention, the best offset behaviour is obtained with those with a hydroxyl number between 10 and 80 and preferably between 20 and 65, and with an acid number between 2 and 25 and preferably between 5 and 15. The products of the present invention have the particular advantage of exhibiting complete inertia towards the ink distribution rollers and towards the blankets which transfer the ink from the plate cylinders to the printing substrate.

The compounds of the present invention should have a viscosity between 2 and 250 poises and preferably between 30 and 200 poises in the case of inks intended for rotary offset and letterpress presses, and a viscosity between 50 and 400 poises and preferably between 130 and 200 poises for sheet-fed offset or letterpress printing inks. The compounds of the present invention, the viscosity of which is lower than 30 poises, optionally mixed with photocopolymerizable monomers and/or oligomers, can be used for the formulation of flexographic, silk screen, and gravure inks.

The following Examples are given for the purpose of illustrating the present invention. All parts are by weight unless otherwise stated.

EXAMPLE 1.

A fraction of the hydroxyl groups of a polyol containing 6 hydroxyl groups per molecule (Pluracol SP760) is first esterified with a fatty monoacid in a double-walled glass reactor with a capacity of 3 liters and equipped with an agitator, a thermometer and an azeotropic distillation column. For this purpose, the following amounts of reactants are introduced into the reactor:
 680 g. of sorbitol- 12 moles ethylene oxide addition product (Pluracol SP760),
 423 g. oleic acid,
 300 g. benzene,
 40 g. p-toluene-sulfonic acid,
 1 g. cuprous oxide.

The mixture is brought to the boil under atmospheric pressure. When 27 ml. of water of esterification have been collected in the course of the azeotropic distillation of the mixture, the latter is cooled to a temperature below 50°C. and the following are added:
 480 g. acrylic acid
 130 g. benzene
 1 g. cuprous oxide The mixture is again brought to the boil and the esterification continued until no further water passes over by azeotropic distillation.

The mixture is cooled and 5 liters of benzene are added, whereupon it is washed in succession with aqueous solutions of sodium chloride and sodium bicarbonate until neutral. 500 ppm hydroquinone are added and the unsaturated ester is isolated by distilling off the solvent in vacuo.

The final product has the following characteristics:
Viscosity: 2.5 poises at 25°C.
OH value: 29
Acid value: 11
Acrylic unsaturation: 3.1 meq./g. (meq. = milliequivalent of acrylic acid)
Coloration: yellow The viscosity was measured with the Hoppler viscosimeter. The acrylic unsaturation was calculated from the intensity of the band at 804 cm$^{-1}$ of the infra-red absorption spectrum, measured in a solution of the product examined in carbon disulfide.

EXAMPLE 2.

The procedure of Example 1 was repeated but the oleic acid was replaced by 220 g. of an addition product of maleic anhydride and oleic acid. This product was obtained by reacting a mixture of 1.2 moles of maleic anhydride with 1 mole of oleic acid at 200°C. for 6 hours in a glass vessel, at atmospheric pressure. Part of the excess of maleic anhydride sublimates during the reaction, the remainder being evaporated at the end thereof. This addition product has an acid number of 385 and has an average maleic anhydride content of 0.7 mole per mole of oleic acid.

The final product, obtained under the experimental conditions of Example 1, has the following characteristics:
Viscosity: 55 poises at 25°C.
OH value: 27
Acid value: 15
Acrylic unsaturation: 4.3 meq./g.

EXAMPLE 3.

The procedure of Example 1 was repeated but the oleic acid was replaced by 750 g. of an addition product of maleic anhydride and linseed oil. This addition product was obtained by heating 1800 g. of linseed oil (iodine number = 190) and 200 g. of maleic anhydride at 250°C. for 4 hours in an autoclave. The iodine number is then 135, the acid number is 110 and the coloration of the product obtained is yellow. The addition product averages 1 mole maleic anhydride per mole of linseed oil.

The final product, obtained under the experimental conditions of Example 1, has the following characteristics:
Viscosity: 72 poises at 25°C.
OH value: 19
Acid value: 7
Acrylic unsaturation: 2.2 meq./g.

EXAMPLE 4.

The oleic acid of Example 1 is replaced by 190 g. of an addition product of maleic anhydride and beta-eleostearic acid. This latter product is obtained by a Diels-Alder reaction according to the process of R. S. Morrell and H. Samuels (J. Chem. Soc. 1932, 2251—54). The reaction is exothermic and takes place readily at 85°–90°C. The product contains one molecule of maleic anhydride per molecule of beta-eleostearic acid and it is in the form of a yellowish-white solid having a melting point of 77°C.

The final product, obtained under the experimental conditions of Example 1, has the following characteristics:
Viscosity: 85 poises at 25°C.
OH value: 25
Acid value: 14
Acrylic unsaturation: 4.7 meq./g.

EXAMPLE 5.

565 g. dimer acid containing 19-22% trimer and 5% monobasic unpolymerized acid (EMPOL 1022 of Emery Industries Inc., see description above)
272 g. pentaerythritol
576 g. acrylic acid
400 g. benzene
20 g. sulfuric acid (d = 1.84)
1 g. cuprous oxide are introduced into a double-walled glass reactor with a capacity of 3 liters and provided with an agitator, a thermometer and an azeotropic distillation column.

The mixture is brought to the boil at atmospheric pressure. The water of esterification resulting from the azeotropic distillation is collected and the benzene is returned to the reactor. Esterification is complete within 7 hours and 144 ml. of water are thus collected; in the course of this period, the boiling temperature of the contents of the flask rises from 92° to 105°C.

This mixture is diluted with 5 liters of benzene and washed in succession with aqueous solutions of sodium chloride and sodium hydrogen-carbonate until neutral. 500 ppm of hydroquinone are then added and the unsaturated ester is isolated by driving off the solvent by distillation in vacuo. Weight obtained: 1280 g., i.e. about 70% of theory.

This ester, of dark brown colour, has the following characteristics:
Viscosity: 600 poises at 25°C.
OH value: 25
acid value: 6
Acrylic unsaturation: 5.5 meq./g.
less than 0.1% by weight of residual benzene.

EXAMPLE 6.

By the procedure of Example 5, an unsaturated ester is prepared from the following constituents:
565 g. dimer acid, same as the one used in Example 5 but less coloured (EMPOL 1038 of Emery Industries Inc., see description above)
408 g. pentaerythritol
720 g. acrylic acid
500 g. benzene
34 g. p-toluene-sulfonic acid
2 g. cuprous oxide There are thus obtained 1740 g. (about 80% of theory) of unsaturated resin which is in the form of a viscous liquid (230 poises at 25°C.), the colour of which is brownish-yellow and which has the following characteristics:
OH value: 30
Acid value: 2
Acrylic unsaturation: 6.5 meq./g.
less than 0.1% of residual benzene.

EXAMPLE 7.

By the procedure of Example 5, an unsaturated ester is prepared from the following components:
565 g. $C_{36}$ dimer acid containing only 3% trimer (EMPOL 1010 of Emery Industries Inc., see description above)
1360 g. of the 1 mole sorbitol- 12 moles ethylene oxide addition product (PLURACOL SP760)
864 g. acrylic acid
500 g. benzene
40 g. p-toluene-sulfonic acid
2 g. cuprous oxide.

The esterification takes 10 hours. The resulting unsaturated resin (1750 g.) has the following characteristics:
Coloration: yellow
Viscosity: 50 poises at 25°C.
OH value: 494
Acid value: 4
Acrylic unsaturation: 4.0 meq./g.

EXAMPLE 8.

In the reactor described in Example 5, pentaerythritol triacrylate is first prepared from the following constituents:
544 g. pentaerythritol
1152 g. acrylic acid
440 g. benzene
40 g. p-toluene-sulfonic acid
2 g. cuprous oxide After 4 hours, the esterification is stopped and the excess of acrylic acid and the benzene are removed from the reaction mixture by passing twice in succession through a thin layer evaporator.

The free hydroxyl group, which still remains in the reaction product obtained in this manner, is reacted with a dimer acid, this operation taking place in the same reactor as was used for the partial esterification. The following are used for this purpose:
660 g. of the crude hydroxylated intermediate product
300 g. dimer acid (EMPOL 1010, see Example 7)
600 g. benzene
1 g. cuprous oxide The esterification is continued for 5 to 6 hours under reflux, whereupon the unsaturated resin obtained in this manner is purified and isolated by the method described in Example 5.

The unsaturated resin (850 g.) has the following characteristics:
Coloration: yelow
Viscosity: 90 poises at 25°C.
OH value: 17
Acid value: 9
Acrylic unsaturation: 7.5 meq./g.

EXAMPLE 9.

a. 1600 g castor oil (containing 3,0 meq. OH/g.) and 400 g maleic anhydride are introduced into the reactor described in Example 5. The mixture is agitated, heated to 125°C. and kept at that temperature for 2 hours to obtain the addition product: castor oil-maleic anhydride (abbreviated as COMA) having a viscosity of 50 poises at 25°C.

b. 417 g. COMA (see above)
375 g. of the 1 mole pentaerythritol + 7 moles ethylene oxide addition product having a molecular weight of about 400 and sold by UGINE-KUHLMAN under the Trade Mark PLURACOL PeP 450
300 g. benzene
30 g. of a 67% aqueous solution of p-toluene-sulfonic acid, and
0.4 g. triphenyl phosphite
are introduced into the same reactor as used in a) above. The mixture is heated to boiling under nitrogen for 3½ hours and 22 ml of esterification water are collected, whereupon the solution is cooled under nitrogen.

c. As soon as the temperature of the solution obtained in b) falls below 50°C., 192 g. acrylic acid and 1 g. cuprous oxide are added and the mixture is again boiled for 10 hours. The temperatur of the mixture reaches 105°C. at the end of the esterification and 40 ml water are collected by distillation. The mixture is purified as in Example 5 and 850 g. of the product having the following characteristics are obtained:
Viscosity at 25°C.: 200 poises
OH value: 42
Acid value: 6.7
Acrylic unsaturation: 2.6 meq./g.
Volatile matter content: < 0.1%

EXAMPLE 10.

a. Into the reactor described in Example 5, the following are introduced:
283 g. dimer acid (EMPOL 1038 of Emery Industries Inc., see Example 6)
73 g. adipic acid
408 g. pentaerythritol
792 g. acrylic acid
600 g. toluene
50 g. of a 67% aqueous solution of p-toluene-sulfonic acid
2 g. cuprous oxide
The mixture is boiled for 5 hours and the temperature finally reaches 116°C. and 235 ml water of distillation are collected. The product is purified as described in Example 5 and 1180 g. of a ready-for-use product having the following characteristics are obtained:
Viscosity at 25°C.: 125 poises
OH value: 12
Acid value: 15
Acrylic unsaturation: 7.6 meq./g.
Volatile matter content: < 0.1% b. If the 73 g. adipic acid of the formulation in a) above are replaced by 194 g. of 1,4,5,6,7,7-hexachlorobicyclo[2.2.1]hept-5-ene-2,3-dicarboxylic acid (HET acid), a product is obtained having the following characteristics:
Viscosity at 25°C.: 440 poises
OH value: 34
Acid value: 12 c. If the 73 g. adipic acid of the formulation in a) above are replaced by 232 g. bromophthalic acid, a product is obtained having the following characteristics:
Viscosity at 25°C.: 275 poises
OH value: 27
Acid value: 8 d. If the 73 g. adipic acid of the formulation in a) above are replaced by 83 g. isophthalic acid, a product is obtained having the following characteristics:
Viscosity at 25°C.: 245 poises
OH value: 40
Acid value: 26

EXAMPLE 11.

a. The following are introduced into the reactor described in Example 5:
102 g. adipic acid
371 g. pentaerythritol
592 g. oleic acid
529 g. acrylic acid
420 g. benzene
42 g. of a 67% aqueous solution of p-toluene-sulfonic acid
1.4 g. cuprous oxide
1.4 g. triphenyl phosphite
The mixture is boiled under nitrogen. Esterification takes 7 hours and the temperature reaches 101°C. and 210 ml. water are collected. The product is purified as in Example 5.
Viscosity at 25°C.: 12 poises b. To 400 g. of the product prepared in a), the following are added:
18 g. of a mixture of 2,4- and 2,6-toluylene-diisocyanate
0.4 g. triethylene diamine
The mixture is heated for one hour at 65°C., whereafter 7 g. n-propanol are added and heating is continued for further 15 minutes. The thus obtained urethanized product has now a viscosity at 25°C. of 140 poises.

EXAMPLE 12.

The esterification is carried out in an enamelled metal reactor with a capacity of 150 liters, equipped with an anchor agitator and an azeotropic distillation column. The reactor is of the double-walled type, with oil heating. The following amounts of reactants are introduced into it:
21.47 kg. dimer acid (EMPOL 1010, see Example 7)
20.67 kg. pentaerythritol
41.04 kg. acrylic acid
20.20 kg. benzene
1.52 kg. p-toluene-sulfonic acid dissolved in 1 kg. of water
0.076 kg. cuprous oxide
0.019 kg. triphenyl phosphite
The mixture is degassed in vacuo to an absolute pressure of 150 mm. Hg., whereupon the pressure is brought back to atmospheric pressure with nitrogen. This operation is repeated three times.

The mixture is brought to boiling temperature under reflux and the water is eliminated. The esterification takes from 7 to 8 hours and, at this moment, 11.47 kg. of water have been azeotropically distilled off.

The mixture is cooled and transferred to a stainless steel vessel with a capacity of 600 liters and provided with a screw agitator. The mixture is diluted with 300 kg. of benzene and washed twice with aqueous solutions of sodium chloride and then three times with aqueous solutions of sodium hydrogen carbonate.

The organic solution purified in this manner is stabilized by adding 70 g. hydroquinone methyl ether, the solvent then being eliminated at a temperature of 50°C. and at a pressure of 150 mm.Hg. in a thin layer evaporator until the residual solvent content is less than 0.1%.

The unsaturated resin of this Example is thus obtained with a yield of about 95% and it has the following characteristics:
Coloration: yellowish-brown
Viscosity: 120 poises at 25°C.
OH value: 24
Acid value: 7
Acrylic unsaturation: 7.5 meq./g.

EXAMPLE 13.

The following materials are introduced into the apparatus described in Example 12:
22.60 kg. dimer acid (EMPOL 1010, see Example 7)
16.32 kg. pentaerythritol
30.80 kg. acrylic acid
20.00 kg. benzene
1.40 kg. p-toluene-sulfonic acid dissolved in 1 kg. water
0.080 kg. cuprous oxide
0.020 kg. triphenyl phosphite After esterification for 8 and a half hours, 9.8 kg. of water have distilled off.

The esterification solution is divided into two equal parts:

The first part (resin No. 13A) is purified by the technique described in Example 12.

To the second part (resin No. 13B) is added a mixture containing 3 kg. ethanol and 3 kg. benzene; the esterification is continued for 3 hours, during which time 0.950 kg. water is distilled off; this second part is then purified by the usual technique.

The two resins thus recovered have the following characteristics:

|  | Resin No. 13A | Resin No. 13B |
|---|---|---|
| Viscosity at 25°C. | 170 poises | 30 poises |
| OH value | 13 | 62 |
| Acid value | 8 | 8 |
| Acrylic unsaturation (meq./g.) | 6.9 | 5.7 |

Treatment by ethanol brought about transesterification, which had the following consequences: reduction of the length of chains, resulting in a lowering of viscosity; producing a more homogeneous molecular weight distribution than that of resin No. 13A, as is demonstrated by comparison of the distribution curves of molecular mass measured by chromatography with gel permeation; increasing the OH number; and slightly reducing the acrylic unsaturation content.

EXAMPLE 14.

A resin is prepared as in Example 12 but the esterification is stopped when an OH number of 48 is achieved. After purification, it has the following characteristics:
Viscosity: 60 poises at 25°C.
OH value: 48
Acid value: 9
Acrylic unsaturation: 7.5 meq./g.

1 kg. of this resin is introduced into a 2 liters double-wall glass reactor equipped with a mechanical agitator and a thermometer, and 47 g. of a mixture of 2,4-and 2.6-toluylene diisocyanate and 1 g. triethylenediamine are added thereto. The temperature is raised to 60°C., while agitating, for one hour. Titration then reveals no further presence of isocyanate groups. The reaction takes place in the air but the reactor is protected against humidity by a silica gel column. The viscosity of the mass increases progressively. The resin obtained has the following characteristics:
Viscosity: 395 poises at 25°C.
OH value: 20
Acid value: 9
Acrylic unsaturation: 7.5 meq./g.

EXAMPLE 15.

a. The following mixture is esterified in the reactor described in Example 12, in the same manner as described there:
11.30 kg. dimer acid (EMPOL 1038, same as in Example 6)
10.88 kg. pentaerythritol
21.00 kg. acrylic acid
10.60 kg. benzene
1.00 kg. of a 67% aqueous solution of p-toluene-sulfonic acid 0.04 kg. cuprous oxide
0.017 kg. triphenyl phosphite The esterification takes 5 hours. The temperature finally reaches 102°C. and 3.95 kg. water of distillation are collected.

After purification, 3.4 kg. of the product having the following characteristics are obtained:
Viscosity at 25°C.: 50 poises
OH value: 84
Acid value: 7.8
Acrylic unsaturation: 8.6 meq/g.

b. The viscosity of the product can be increased by urethanization with different isocyanates. 1000 g. of the product obtained in a) hereinabove and 0.5 g. triethylene diamine are reacted with the amounts of the isocyanates given in the following Table II. The mixture is heated to 70°C. until disappearance of the isocyanate groups, which takes about one hour.

TABLE II

| product No. | amount of isocyanate in g. per 1000 g. of product a) + 0.5 g. triethylene diamine | viscosity in poises at 25°C. | OH index |
|---|---|---|---|
| b 1 | 110 g. phenyl-isocyanate | 210 | 36 |
| b 2 | 37.3 g. toluylene-diisocyanate | 195 | 80 |
| b 3 | 48.8 g. hexamethylene-diisocyanate | 210 | 55 |
| b 4 | 46.5 g. diphenylmethane-diisocyanate | 220 | 50 |
| b 5 | 67.2 toluylene-diisocyanate + | | |

TABLE II-continued

| product No. | amount of isocyanate in g. per 1000 g. of product a) + 0.5 g. triethylene diamine | viscosity in poises at 25°C. | OH index |
|---|---|---|---|
| b 6 | 44.8 g. 2-hydroxyethyl acrylate 72.1 g. toluylene-diisocyanate + 30.7 g. n-butanol | 220 215 | 58 52 |

EXAMPLE 16.

A mixture of 100 parts of the resin of Example 1 and 1 part of azobisisobutyronitrile are poured into a "Teflon" (polytetrafluorethylene) dish, the depth of which is 1 mm.

A sheet of bioriented polyethylene terephthalate with a thickness of 12 micron is placed in contact with the solution in order to protect the latter from the air. The dish is placed in a stove at 80°C. After 25 minutes, hardening is complete. The polymer is insoluble in the usual solvents. After extraction with methyl ethyl ketone in a Soxhlet apparatus, a residue of 96.4% remains.

EXAMPLE 17.

The following two mixtures are prepared from the resin of Example 5:

Mixture A :
 10 parts of the resin of Example 5
 0.3 part of a 50% solution of benzoyl peroxide in dioctyl phthalate
 0.02 part of a paraffin having a melting point of 52-54°C.

Mixture B :
 10 parts of the aforesaid resin
 0.3 part of a 10% solution of dimethyl-p-toluidine in butyl acrylate
 0.02 part of the aforesaid paraffin.

After rapidly mixing compositions A and B, a 500 micron film is applied to a glass plate by means of a hand coater. After a few minutes, the reaction starts at ambient temperature and the paraffin floats on the surface. After 15 minutes, a hard, non-sticky film is obtained.

EXAMPLE 18.

A film with a thickness of 500 microns is poured on to a glass plate from the unsaturated resin of Example 7, to which 0.5% by weight of benzoin methyl ether has been added.

This glass plate is placed in a tight box provided with a window composed of a sheet of bioriented polyethylene terephthalate with a thickness of 12 microns. Air is flushed out by passing in a current of nitrogen for 10 minutes, followed by irradiation with a Philips HTQ-4 1000 Watt ultraviolet lamp placed at a distance of 25 cm.

After ultra-violet irradiation of 1 minute, the resin is perfectly hardened (96.5% insoluble in methyl ethyl ketone).

EXAMPLE 19.

A film of the unsaturated resin of Example 8, with a thickness of 100 microns, is poured on to a glass plate. This film is hardened by electron beam curing under the following conditions:
 Electron accelerator: type BBC, 300 KeV, 50 mA
 Dose rate: 10 Mrad/sec.

Irradiation in an inert atmosphere obtained by flushing the surface with combustion gases.

The film is perfectly hardened (more than 98% insoluble in methyl ethyl ketone) with a dose of 1 Mrad, which represents a linear speed of the film of 70 meters per minute.

EXAMPLE 20. FORMULATION FOR ROAD MARKING.

A paint is prepared from the following constituents:
 1000 parts of the unsaturated resin of Example 13B
 500 parts methyl methacrylate 370 parts ethyl acrylate 130 parts acrylic acid
 4 parts paraffin, melting point 52-54°C.
 2500 parts calcium carbonate, and 1000 parts titanium oxide.

From this paint, the following two compositions are prepared:

Composition A:
 500 parts of the aforesaid paint
 10 parts of a 50% solution of benzoyl peroxide in dioctyl phthalate Composition B:
 500 parts of the aforesaid paint
 10 parts of a 10% solution of dimethyl-p-toluidine in ethyl acrylate.

These two compositions are applied simultaneously and in equal amounts by means of a two-head spray gun, in bands of a thickness of 250 microns, on to concrete and asphalt.

Hardening at ambient temperature is obtained in 10 minutes. Adhesion to the two substrates is excellent. The pencil hardness is higher than 4 H. After 6 months, in the winter season, the painted surfaces are still intact.

EXAMPLE 21. POLYVINYL CHLORIDE PLASTISOL.

A polyvinyl chloride plastisol is prepared by mixing:
 100 parts of polyvinyl chloride obtained by polymerization in aqueous suspension and having a molecular weight of 19,000
 25 parts of the resin of Example 12,
 4 parts of dibutyl-tin maleate,
 20 parts titanium oxide,
 50 parts chalk,
 1 part colloidal silica (Aerosil 200, Degussa), and
 1 part t-butyl hydroperoxide.

This mixture is applied to a metal sheet at a thickness of 40 microns and heated for 10 minutes at 160°C. 100% adhesion (cross-cut), a pencil hardness of HB and an Erichsen slow penetration test value of 8 mm. are obtained.

EXAMPLE 22. ANAEROBIC ADHESIVE.

100 parts of the resin of Example 7 are mixed with 30 parts of the resin of Example 1. 2 parts cumene hydroperoxide, 0.3 parts dimethylaniline, 0.2 parts benzoyl sulfimide and 0.015 part hydroquinone are added. The mixture has an initial viscosity of 22 poises; it is saturated with oxygen and kept in a thin-walled polyethylene container. During periods 3 and 6 months, the viscosity increases to 25 and 32 poises, respectively.

The same product, stored in a glass container with the exclusion of air, after flushing with nitrogen, polymerizes within 5 days (viscosity > 20,000 poises).

4 drops of the 22-poise mixture are applied to the threaded portion of a series of standard 10 mm. bolts, which were then screwed by hand into a locknut. After 30 minutes, the connection cannot be unscrewed and after 3 hours at 22°C. an unlocking torque of 0.64 m./kg. is measured.

EXAMPLE 23. METAL VARNISH.

An ultra-violet varnish, which can be applied to a metal sheet, is obtained by mixing:

70 parts of the unsaturated resin of Example 8
27 parts Tercarol 1 triacrylate (TERCAROL 1 is a Registered Trade Mark for the addition product of 12 moles propylene oxide on one mole of glycerol, having a molecular weight of about 1000)
3 parts of 2-hydroxyethyl acrylate monomaleate
40 parts ethyl acrylate
5 parts diethylene glycol diacrylate
0.5 parts colloidal silica (AEROSIL 200 - Degussa)
1 part PA-520 polyethylene wax (Hoechst) and
3 parts of a mixture of benzoin butyl ether isomers (Trigonal-14; Noury-Lande).

A layer of 22 grams per square meter of the composition is applied on to a degreased tin plate sheet by means of a roller coater. The sheet is moved at a speed of 0.5 meters per minute under an ultra-violet lamp of the Hanovia type, placed at right angles at a distance of 7.5 cm. from the sheet and having a power of 80 Watts per cm. The varnish applied in this manner becomes hard and non-sticky (pencil hardness: 2H; 97% insoluble in methyl ethyl ketone; cross-cut adhesion test 100%).

EXAMPLE 24. PREPARATION OF AN ULTRA-VIOLET SEALER SUITABLE FOR APPLICATION TO CHIP BOARD.

A sealer of the following composition is prepared in a Werner type kneader:

40 parts of the unsaturated resin of Example 13B
0.2 part of a mixture of benzoin butyl ether isomers (Trigonal-14, see Example 23)
5.0 parts microtalc extra
7.8 parts barium sulfate, and
47 parts calcium sulfate (Leichtspat FFF, of Harzer Gipswerke).

This composition is applied to chip boards in a layer of 150 grams per square meter by means of a reverse roll coater.

After ultra-violet irradiation for a period of 30 seconds under a Philips HTQ4 lamp at a distance of 25 cm., the boards have a hard surface (Persoz hardness 120 seconds) and can be sanded.

EXAMPLE 25. VARNISH.

A varnish, which can be cured by an accelerated electron beam, is prepared from the following constituents:

70 parts of the unsaturated resin of Example 8
27 parts 1,4-butanediol diacrylate
0.5 part of colloidal silica (AEROSIL 200 - DEGUSSA), and
2.5 parts silica (SYLOID 74 made by Grace).

This varnish is applied to a glass plate in a coat of a thickness of 50 microns by means of a hand coater. With a dose of 1 Mrad (irradiation conditions identical to those of Example 19), the pencil hardness is equal to 5H and the product is insoluble in methyl ethyl ketone to an extent of 96.9%.

EXAMPLE 26. PAINT

A paint which can be applied by a curtain coater and which can be cured by an accelerated electron beam is prepared from the following constituents:

15 parts of the unsaturated polyester described below
20 parts of the unsaturated resin of Example 13B
15 parts 1,4-butanediol acrylate
43 parts titanium oxide
4 parts Shepperd Brown 49 dye, and
3 parts silica (SYLOID 74 made by GRACE).

The unsaturated polyester used in this composition was obtained by condensation of a mixture of maleic anhydride, adipic acid, ethylene glycol, dipropylene glycol, and 2-ethylhexyl alcohol in a molar ratio of 0.4 : 0.6 : 0.8 : 0.2 : 0.1.

This composition forms a very stable "curtain", giving off no odour. It is applied in coats of 120 grams per square meter on to chip board panels previously treated with a stopper and carefully sanded. Irradiation with an electronic beam is effected under the conditions of Example 19. The dose necessary for perfect curing is 2 Mrad, which represents a linear speed of the film of 35 meters per minute. The appearance of the panels is excellent. The paint is glossy and very hard (Pencil hardness: 3 H), its resistance to water and solvents is excellent and its appearance is unchanged after 500 hours exposure to the Weather-O-matic device.

EXAMPLE 27. PAINT.

A paint which can be applied by a roller coater and cured by an electron beam is prepared from the following constituents:

20 parts of the unsaturated resin of Example 12
12 parts of an unsaturated resin of the polyether acrylate-urethane type described below
10 parts of an oligomer of the Tercarol-1 triacrylate type (described in Example 23)
12 parts 1,4-butanediol diacrylate
20 parts titanium oxide
22 parts chalk
3 parts silica (SYLOID 74), and
1 part colloidal silica (AEROSIL 200).

A coat of 52 grams per square meter is applied by a roller coater to a rigid fibre board (60 × 30 cm.) previously treated with a glycerophthalic sealer.

After irradiation under the conditions described in Example 19 (2 Mrad) and at a linear speed of 35 meters per minute, a coating is obtained which has a glossy finish and a pencil hardness of 4 H.

The unsaturated resin of the polyether acrylate-urethane type used in the composition of this Example was obtained by reacting 3 moles of polypropylene glycol with 4 moles of isophorone diisocyanate and 2 moles of hydroxyethyl acrylate in the presence of 2% by weight (calculated with reference to the diisocyanate) of triethylenediamine, at 80°C. for 10 hours, until the diisocyanate bands in the infra-red spectrum disappeared.

EXAMPLE 28.

A mixture of:

68 parts of the product of Example 12
27 parts trimethylolpropane triacrylate
2 parts acrylic acid, and
3 parts benzoin ethyl ether is applied at the rate of 3 grams per square meter with the aid of a reverse roller coater to the face of a polyethylene film which had been treated by corona effect. A film of aluminium is then applied to the coated face.

The laminate is passed under a Hanovia lamp (80 Watts/cm.), with the polyethylene face turned towards the lamp, at a speed of 200 meters per minute. After ageing for 10 minutes it is no longer possible to separate the two films without tearing the aluminium foil.

EXAMPLE 29. OFFSET INK FOR WEB PRESS.

This is prepared from the following constituents:
15 parts phthalocyanine blue (Colour Index, Pigment Blue 15)
64 parts of the unsaturated resin of Example 12
10 parts of trimethylolpropane triacrylate
5 parts dioctyl phthalate
5 parts benzoin butylether, and
1 part polyethylene wax PA-520 (HOECHST).

This ink is applied at a thickness of about 1 micron to a strip of paper. The latter is then passed, at variable speeds and at a distance of 7.5 cm., under a Hanovia No. 6525 A 431 type ultra-violet lamp of 62.5 cm. arc length and a power of 5000 Watts (medium pressure mercury lamp), Offsetting appears at 4 meters per second and the hardened ink becomes unscratchable two hours after irradiation.

In four-colour printing on a rotary press equipped with three lamps of the type described, the ink dries at a speed of 310 meters per minute.

EXAMPLE 30. OFFSET INK FOR WEB PRESS.

An ink is prepared from the following constituents:
15 parts phthalocyanine blue (Colour Index, Pigment Blue 15)
59 parts of the unsaturated resin of Example 12
15 parts of the unsaturated resin of Example 13B
5 parts dioctyl phthalate
5 parts of a mixture of benzophenone and Michler's ketone in the weight ratio 6:1, and
1 part polyethylene wax PA-520 (HOECHST).

This ink has a reactivity similar to that of Example 29.

EXAMPLE 31. OFFSET INK FOR SHEET-FED MACHINES.

An ink is prepared from the following constituents:
16 parts AAMX benzidine yellow (Colour Index, Pigment Yellow 13)
70 parts of the unsaturated resin of Example 6
4 parts trimethylolpropane triacrylate
5 parts dioctyl phthalate
4 parts 1-phenyl-1,2-propanedione 2-[O-(benzoyl)oxime], and
1 part polyethylene wax PA-520 (HOECHST).

The appearance of offsetting determined as in Example 29 occurs at 3.5-4 meters per second.

In four-colour printing on a sheet-fed press equipped with three ultra-violet lamps of 80 Watts per centimeter, it was possible to work at the rate of 8,000 sheets per hour.

EXAMPLE 32. OFFSET INK FOR SHEET-FED MACHINE.

An ink is prepared from the following constituents:
16 parts AAMX benzidine yellow (Colour Index, Pigment Yellow 13)
50 parts of the unsaturated resin of Example 14
24 parts of the unsaturated resin of Example 13B
5 parts dioctyl phthalate
5 parts of a mixture of benzophenone and Michler's ketone in the weight ratio 6:1, and
1 part polyethylene wax PA-520.

This ink has a reactivity similar to that of Example 31.

EXAMPLE 33.

Yellow UV-curable inks are prepared from the following constituents:
16 parts AAMX benzidine yellow (Colour Index, Pigment Yellow 13)
70 parts of one of the various binders given in Table III below
4 parts trimethylolpropane triacrylate
4 parts dioctyl phthalate
5 parts of a mixture of benzophenone and Michler's ketone in the weight ratio 6:1, and
1 part polyethylene wax PA-520.

The appearance of offsetting is determined as in Example 29.

TABLE III

| Formulation of the UV ink with the binder of Example | Speed of passing under the UV lamp (m/second), at which offsetting appears |
|---|---|
| 9 | 1.75 |
| 10 a | 3.25 |
| 10 b | >4 |
| 10 c | >4 |
| 10 d | 3.50 |
| 11 b | 2.5 |
| 15 a | 2.25 |
| 15 b 1 | 1.75 |
| 15 b 2 | 2.5 |
| 15 b 3 | 3.0 |
| 15 b 4 | 3.0 |
| 15 b 5 | 2.75 |
| 15 b 6 | 2.5 |

EXAMPLE 34.

In the yellow ink of Example 33 prepared with the binder of Example 15 a (non-urethanized), the 4 parts trimethylolpropane triacrylate and the 4 parts dioctyl phthalate are replaced by 8 parts N-methyl-diethanolamine diacrylate.

Offsetting appears then at 3.25 m./second (gain of 1 m./second).

EXAMPLE 35. FLEXOGRAPHIC INK.

This is prepared from the following constituents:
6 parts phthalocyanine blue (Colour Index, Pigment Blue 15)
45 parts of the unsaturated resin of Example 13B
30 parts 1,4-butane-diol diacrylate
10 parts N-methyl-diethanolamine diacrylate
8 parts of a mixture of benzophenone and Michler's ketone in the weight ratio 6:1, and
1 part polyethylene wax PA-520.

Offsetting, determined as in Example 29, appears at 1.75 m./second.

Application of 5 microns films is carried out with a bar-coater on the following substrates
nitrocellulose varnished aluminium foil
nitrocellulose varnished Cellophane MS
polyvinylidene chloride (solution) varnished Cellophane $XS_1$
polyvinylidene chloride (emulsion) varnished Cellophane $XS_2$ polyethylene treated by corona effect.

Drying under a UV lamp (as described in Example 29) is satisfactory at more than 180 meters per minute. There is no offsetting between print and substrate nor any print to print sticking. The film is glossy. Adhesion, determined by the Scotch tape test, is satisfactory and the resistence to nail-scratching and rubbing are good.

EXAMPLE 36. WHITE OFF-SET INK FOR METAL DECORATION.

It has the following composition
55 parts surface-treated rutile titanium oxide
35 parts of the unsaturated resin prepared in Example 15b2
2 parts dioctyl phthalate
8 parts of a mixture of benzophenone and Michler's ketone in the weight ratio 6:1.

Printing is carried out on an off-set press for tin plate decoration. Drying takes place by means of 3 medium pressure mercury vapor, air-cooled, 80 Watts per centimeter arc length, UV lamps. Speed of printing is 5,000 sheets per hour. The drying and adhesion properties allow stacking, pile stockage, handling of the iron plate stacks and uptake for the supply of presses and varnishers, which realize the subsequent colour printing and varnishing of the tin plates.

We claim:
1. Compounds with multiple acrylic radicals, the average composition of which has the general formula
$$X \cdot [Y \cdot (Z)_{m-p-l}]_n$$
wherein X is the radical derived by removing the OH groups from the carboxyl groups of an organic carboxylic acid containing n COOH groups and the number of carbon atoms of which is between 14 and 90,
Y is the radical derived by removing m-p hydrogen atoms from the hydroxyl groups of an organic compound containing m OH groups,
Z is the monovalent radical derived by removing the OH group from the carboxyl group of a monocarboxylic acid having at least one terminal $CH_2=CH-COO-$ radical,
n is a whole number from 1 to 6,
m is a whole number from 2 to 8,
p is a number of from 0 to 2.5, with the proviso that m-p-l is a positive number different from zero and that n(m-p-l) is between 2 and 15.
2. Compounds according to claim 1, in which X is the radical derived from an organic carboxylic acid having from 18 to 54 carbon atoms, n is a whole number of from 1 to 4 and m is a whole number of from 3 to 6.
3. Compounds according to claim 1, in which X is the radical derived from an organic aliphatic monocarboxylic acid.
4. Compounds according to claim 1, in which X is the radical derived from an organic polycarboxylic acid.
5. Compounds according to claim 1, in which X is the radical derived from a mixture of at least 25 mole % of an organic carboxylic acid having from 14 to 90 carbon atoms and at most 75 mole % of at least one organic aliphatic, cycloaliphatic or aromatic carboxylic acid having less than 14 carbon atoms.
6. Compounds according to claim 1, in which Y is the radical derived from an organic compound selected from the group consisting of an aliphatic polyhydric alcohol, an oxyalkylated aliphatic polyhydric alcohol, a polyester-alcohol, a polyether-alcohol, an oxyalkylated polyester-alcohol and an alkoxylated polyether-alcohol.
7. Compounds according to claim 1, in which Z is the radical derived from a monocarboxylic acid selected from the group consisting of acrylic acid, an ester of one mole of a hydroxyalkyl acrylate with one mole of a dicarboxylic acid or anhydride, an ester of two moles of a hydroxyalkyl acrylate with one mole of a tricarboxylic acid and an ester of three moles of a hydroxylalkyl acrylate with one mole of a tetracarboxylic aicd, the alkyl radical of said hydroxyalkyl acrylates having from 2 to 12 carbon atoms.
8. A compound with multiple acrylic radicals selected from the group consisting of: the reaction product of 1 mole of ricinoleic acid with 1 mole of trimethylolpropane and 3 moles of acrylic acid; the reaction product of 1 mole of stearic acid with 1 mole of sorbitol and 5 moles of the ester of 1 mole of adipic acid with 1 mole of hydroxyethyl acrylate; the reaction product of 1 mole of oleic acid with 1 mole of dipentaerythritol and 5 moles of the ester of 1 mole of maleic anhydride with 1 mole of hydroxyethyl acrylate; the reaction product of 1 mole of linseed oil fatty acid with 1 mole of the addition product of about 12 moles of ethylene oxide with 1 mole of sorbitol and 5 moles of the ester of 1 mole of phthalic anhydride with 1 mole of hydroxyethyl acrylate; the reaction product of 1 mole of $C_{36}$ dimer acid with 2 moles of pentaerythritol and 6 moles of acrylic acid; the reaction product of 1 mole of $C_{36}$ dimer acid with 2 moles of the addition product of 3 moles of propylene oxide with 1 mole of glycerol and 4 moles of acrylic acid; the reaction product of 1 mole of the addition product of maleic anhydride on 9,12-linoleic acid with 3 moles of ethylene glycol and 3 moles of the ester of 1 mole of maleic anhydride with 1 mole of 2-hydroxypropyl acrylate; the reaction product of 1 mole of the ester of 1 mole of pyromellitic acid and 4 moles of ricinoleic acid, with 4 moles of trimethylolpropane and 8 moles of acrylic acid; the reaction product of 1 mole of $C_{36}$ dimer acid with 2 moles of the addition product of 12 moles of ethylene oxide with 1 mole of glycerol and 4 moles of the ester of 1 mole of maleic anhydride with 1 mole of hydroxyethyl acrylate; the reaction product of 1 mole of $C_{36}$ dimer acid chloride with 2 moles of pentaerythritol and 6 moles of acrylyl chloride; the reaction product of 1 mole of the addition product of maleic anhydride on 9,12-linoleic acid with 3 moles of the addition product of 3 moles of propylene oxide with 1 mole of glycerol and 3 moles of acrylic anhydride; the reaction product of 1 mole of the dimer of methyl linoleate with 2 moles of glycerol and 4 moles of ethyl acrylate; the reaction product of 1 mole of oleic acid with 1 mole of the addition product of 12 moles of ethylene oxide with 1 mole of sorbitol and 5 moles of acrylic acid; the reaction product of 1 mole of stearic acid with 1 mole of the addition product of 7 moles ethylene oxide with 1 mole pentaerythritol and 3 moles of the ester of 1 mole of maleic anhydride with 1 mole of hydroxyethyl acrylate; the reaction product of 1 mole of the addition product of 2 moles of thioglycolic acid on 1 mole of linolenic acid with 3 moles of polyethylene glycol and 3 moles of acrylic acid; the reaction product of 1 mole of the addition product of maleic anhydride on oleic acid with 3 moles of the addition product of 12 moles of ethylene oxide with 1 mole sorbitol and 15 moles of acrylic acid; the reaction product of 1 mole of the addition product of maleic anhydride on linseed oil with 2 moles of the addition product of 12 moles of ethylene oxide with 1 mole of sorbitol and 10 moles of acrylic acid; the reaction product of 1 mole of the addition product of maleic anhydride on beta-eleostearic acid with 3 moles of the addition product of 12 moles of ethylene oxide with 1 mole of sorbitol and 15 moles of acrylic acid; the reaction product of 1 mole of $C_{36}$ dimer acid with 2 moles of the addition product of 12 moles of ethylene oxide with 1 mole of sorbitol and 10 moles of acrylic acid; the reaction product of 1 mole of the addition product of maleic anhydride on castor oil with 2 moles of the addition product of 7 moles of ethylene oxide with 1 mole of pentaerythritol and 6 moles of acrylic acid; the reaction product of 0.5 mole of $C_{36}$ dimer acid and 0.5 mole of adipic acid with 2 moles of pentaerythritol and 6 moles of acrylic acid; the reaction product of 0.5 mole of $C_{36}$ dimer acid and 0.5 mole of 1,4,5,6,7,7-hexachlorobicyclo[2.2.1]hept-5-ene-2,3-dicarboxylic acid with 2 moles of pentaerythritol and 6 moles of acrylic acid; the reaction product of 0.5 mole of $C_{36}$ dimer acid and 0.5 mole of tetrabromophthalic anhydride with 2 moles of pentaerythritol and 6 moles of acrylic acid; and the reaction product of 0.5 mole of $C_{36}$ dimer acid and 0.5 mole of isophthalic acid with 2 moles of pentaerythritol and 6 moles of acrylic acid.

9. A process for the preparation of compounds with multiple acrylic radicals, the average composition of which has the general formula

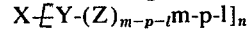

wherein X is the radical derived by removing the OH groups from the carboxyl groups of an organic carboxylic acid containing n COOH groups and the number of carbon atoms of which is between 14 and 90, Y is the radical derived by removing m-p hydrogen atoms from the hydroxyl groups of an organic compound containing m OH groups, Z is the monovalent radical derived by removing the OH group from the carboxyl group of a monocarboxylic acid having at least one terminal $CH_2=CH-COO-$ radical, n is a whole number from 1 to 6, m is a whole number from 2 to 8, p is a number of from 0 to 2.5, with the proviso that m-p-1 is a positive number different from zero and that n(m-p-1) is between 2 and 15, which comprises reacting together 1 mole of an organic carboxylic acid of the formule $X(OH)_n$, n moles of an organic compound of the formula $YH_m$ and n(m-1) moles of an organic monocarboxylic acid of the formula ZOH having at least one terminal $CH_2=CH-COO-$ radical, X, Y, Z, n and m having the meanings given above, the reaction being carried out in the presence of an esterification catalyst, at atmospheric pressure and at a temperature of from about 70°C. to 140°C., for a period of from 2 to 10 hours.

10. A two step embodiment of the process according to claim 9, which comprises esterifying, in a first step, the organic compound $YH_m$ with the organic carboxylic acid $X(OH)_n$ and then esterifying in a second step the obtained hydroxy ester $X(YH_{m-1})_n$ with the organic monocarboxylic acid ZOH.

11. A two step embodiment of the process according to claim 9, which comprises esterifying, in a first step, the organic compound $YH_m$ with the organic monocarboxylic acid ZOH and subsequently esterifying in a second step the obtained hydroxy ester $Y(H)-Z_{m-1}$ with the organic carboxylic acid $X(OH)_n$.

12. A process for decreasing the viscosity of the compounds according to claim 1, wherein said compounds are partially transesterified with an organic hydroxy compound having a molecular weight lower than 200.

13. The process of claim 12, wherein the hydroxy compound is an aliphatic monohydric alcohol, an aliphatic polyhydric alcohol or a hydroxyalkyl acrylate.

14. A process for the preparation of a polymer of the compounds with multiple acrylic radicals according to claim 1, which comprises heating said compounds at a temperature of from 50°C. to 250°C., in the absence of oxygen.

15. The process of claim 14, in which the heating is carried out at a temperature of from 50° to 150°C.

16. The compound of claim 8 which is the reaction product of 0.5 mol of $C_{36}$ dimer acid and 0.5 mol of adipic acid with 2 mols of pentaerythritol and 6 mols of acrylic acid.

* * * * *